United States Patent [19]

Persidsky et al.

[11] 4,268,393

[45] May 19, 1981

[54] APPARATUS FOR CENTRIFUGAL SEPARATION OF PLATELET-RICH PLASMA

[75] Inventors: Maxim D. Persidsky, San Francisco; Nan-Sing Ling, San Rafael, both of Calif.

[73] Assignee: The Institutes of Medical Sciences, San Francisco, Calif.

[21] Appl. No.: 146,462

[22] Filed: May 5, 1980

[51] Int. Cl.³ .............................................. B01D 21/26
[52] U.S. Cl. ............................... 210/516; 128/214 D; 233/26; 206/568; 210/927
[58] Field of Search ....... 210/516, DIG. 23, DIG. 24, 210/78, 83, 359; 206/568, 570, 828; 233/26; 128/214 D

[56] References Cited

U.S. PATENT DOCUMENTS

| | | | |
|---|---|---|---|
| 3,800,947 | 4/1974 | Smith | 210/DIG. 23 |
| 3,830,425 | 8/1974 | Stallmann | 233/26 |
| 3,960,727 | 6/1976 | Hochstrasser | 210/78 |
| 3,986,506 | 10/1976 | Garber et al. | 128/214 D |
| 4,007,871 | 2/1977 | Jones et al. | 210/DIG. 23 |
| 4,057,499 | 11/1977 | Buono | 210/516 |
| 4,213,561 | 7/1980 | Bayham | 233/26 |

OTHER PUBLICATIONS

Persidsky et al., "Separation of Platelets by Modified Centrifugal Elutriation System", Blood, vol. 52, #5 Supp. 1, p. 170; Nov. 1978.
Persidsky et al., "Separation of Platelets by Centrifugal Elutriation", Cryobiology, vol. 14, p. 700, (1977).

Primary Examiner—Benoît Castel
Attorney, Agent, or Firm—Limbach, Limbach & Sutton

[57] ABSTRACT

This invention relates to an apparatus for separating platelets from blood samples by subjecting the blood sample to centrifugal force in the chamber while displacing the platelets from the blood sample by injecting a relatively small volume of saline into the centrifugally outer end of the chamber. In the preferred apparatus, the saline is injected into the blood sample by driving the chamber supporting the blood sample against a saline filled collapsible cavity under the influence of centrifugal force.

3 Claims, 11 Drawing Figures

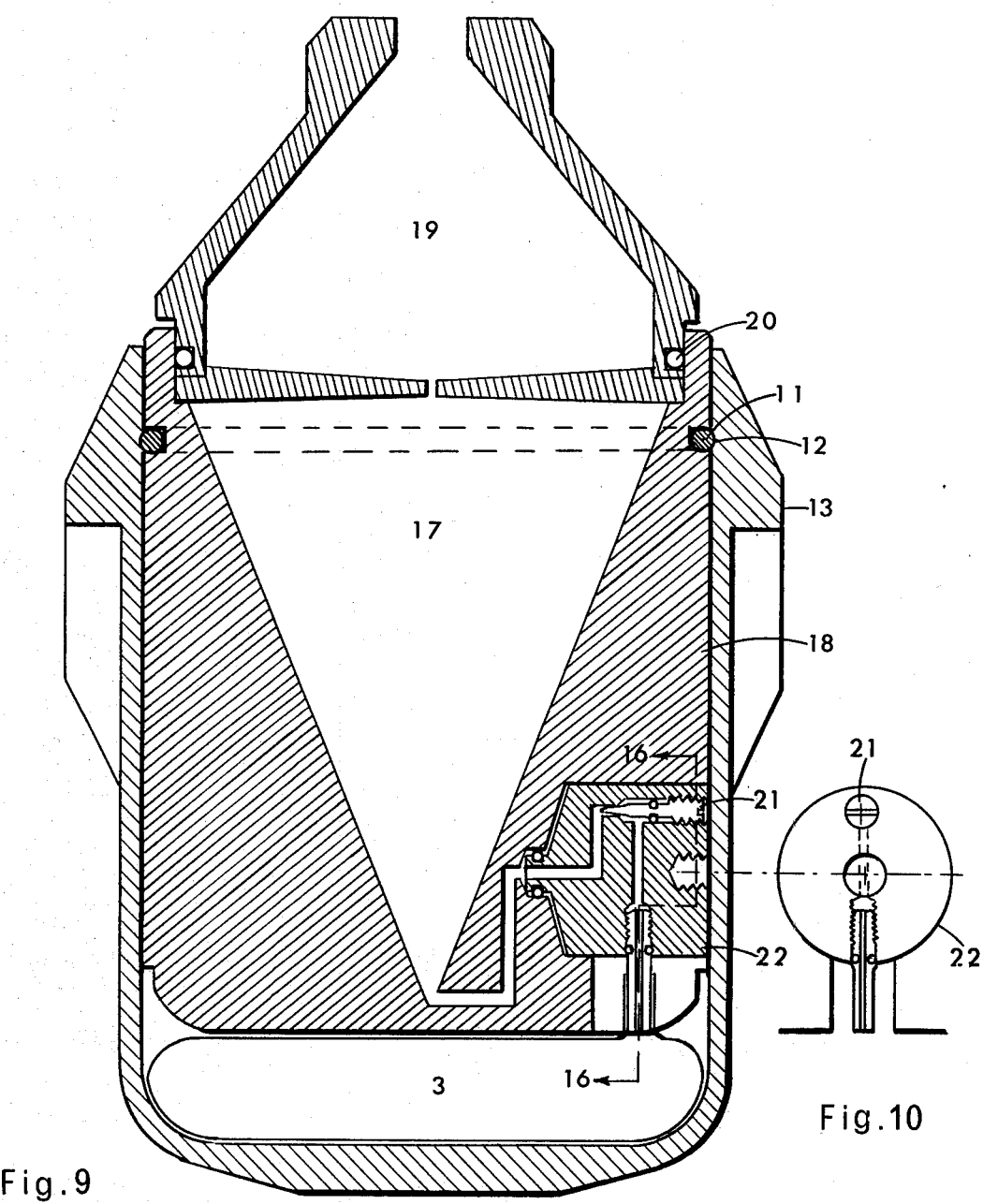
Fig. 9
Fig. 10
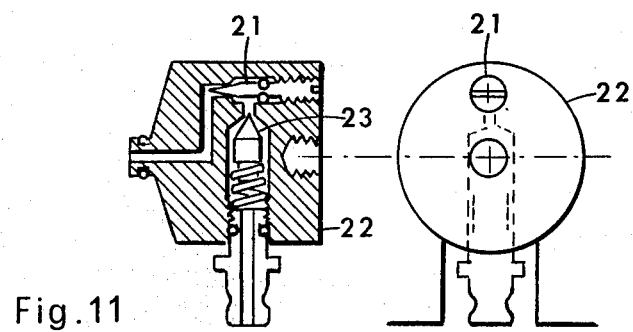
Fig. 11

APPARATUS FOR CENTRIFUGAL SEPARATION OF PLATELET-RICH PLASMA

The invention described herein was made in the course of work under a grant or award from the Department of Health, Education, and Welfare.

BACKGROUND OF INVENTION

This invention relates to a device for the separation of platelet rich plasma from whole blood. The invention represents an adaptation to the platelet transfusion service of the process and a device disclosed in the copending application by Maxim D. Persidsky entitled Process and Device for Centrifugal Separation of Platelets.

According to this device the separation of dissimilar solid particles, such as platelets and other blood cells, is effected by holding red and white blood cells with the aid of centrifugal force at a steady state equilibrium in a chamber, preferably of a conical shape, while displacing platelet rich plasma (PRP) with an equivalent volume of normal saline which is filtering through the suspension of blood cells in the direction generally against the centrifugal force. The liquid medium enters the conical chamber at its vertex which is oriented away from the center of rotation, thereby being at the centrifugal outer end of the chamber, while PRP exits the chamber through its base, which is the centrifugal inner end of the chamber. The liquid flow is generated by means of a piston pump in response to centrifugal force. The apparatus is designed as an insert to be used in a centrifuge swinging bucket, and consists of a cylinder and a piston, the latter incorporating both the conical separation chamber at its lower end and the PRP receiving chamber at its upper end. There is a needle valve in the piston controlling the flow rate of the medium flowing from the cylinder through the passageway leading to the conical chamber's centrifugal outer end. To prevent an immediate discharge of blood cells from the conical chamber by the flow of saline at the start of centrifugation, a control means is provided for holding movement of the piston into the cylinder until a maximum centrifugal force is applied. The control means comprises an o-ring on the piston received in a groove in the wall of the cylinder. This provision allows one to clear blood cells from the centripetal end of the chamber by sedimenting cells at a low centrifugal speed applied for one minute after which centrifugal speed is raised to a required higher value at which the o-ring snaps from the groove and the piston begins to force medium from the cylinder into the conical chamber.

SUMMARY OF INVENTION

The principal object of this invention is to provide a self-contained system, as described above, for the effective collection of PRP from whole blood, preferably from the same donor, free of other blood cells and in a quantity and quality compatible with the requirements practiced in blood banks and in hospitals. To provide a totally sealed, disposable, low-cost system consisting of three interconnected collapsible plastic bags, held together in a rigid support which is fitted into a centrifuge bucket. More particularly, to provide a system of three bags consisting of the middle bag, preferably conical in shape, filled with blood and functioning as a separation chamber; the lower bag holding normal saline for displacement of PRP from the middle bag; and the upper bag for receiving PRP displaced from the middle bag. Also, to provide a system which is sterile and incorporates the means for an aseptic handling during all the procedural steps.

Another object of this invention is to provide the means for delaying the start of the fluid flow during the beginning of centrifugation for about a minute in order to allow initial clearance at the top of the chamber from red and white blood cells as described above. This is accomplished either by an elastic o-ring fixed around the plunger and a groove on the inner wall of the cylinder which retains the o-ring in place until the centrifugal force reaches a certain prescribed value, or by installing a spring-loaded valve which will open only at a certain prescribed g-force.

DETAILED DESCRIPTION

Referring now to the accompanying drawings:

FIG. 9 is a vertical section of another version of the scaled-up platelets separation device taken along the vertical central axis and showing means for regulating flow rate and for disconnecting collapsible bag.

FIG. 10 is a fragmentary cross-section through a modular insert incorporating a needle valve for the regulation of flow rate and a connecting nipple, and taken along the lines 16 and 16 shown in FIG. 9.

FIG. 11 is a fragmentary cross-section through a modular insert incorporating a needle valve for regulating flow rate and the spring loaded valve activated by centrifugal force.

Figure 1:
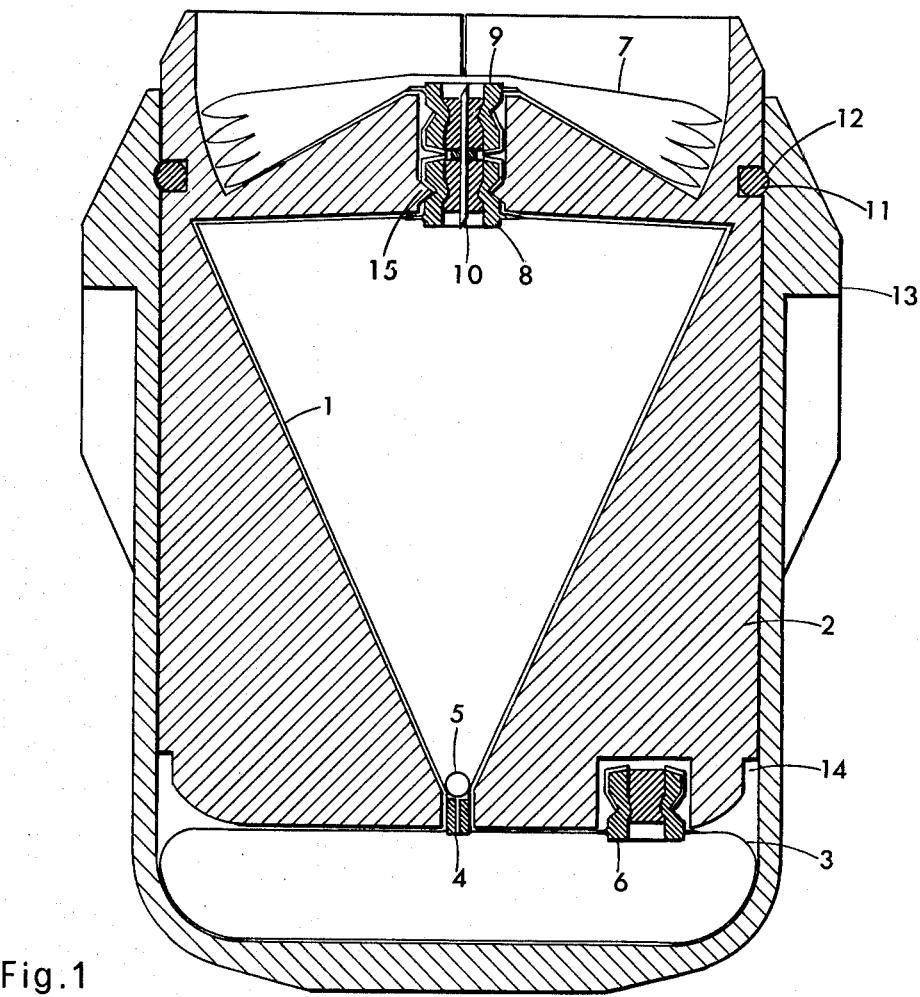
FIG. 1 is a vertical section of the scaled-up version of the apparatus taken along the vertical central axis and showing the apparatus consisting of three collapsible bags inserted into the centrifuge bucket.

The apparatus shown in FIG. 1 and FIG. 2 through FIG. 8 represents a scaled-up for clinical use version of the system disclosed in the copending application by Maxim D. Persidsky and represented in FIGS. 3 and 4. It is designed as a disposable system consisting of three collapsible bags which are completely sealed and will allow one to maintain sterility during all the steps of the operation. Thus, the system is designed to comply with the FDA requirements of safety for human use. This system consists of a conical bag 1 functioning as a separation chamber which is held in a rigid support 2 split into two halves (FIG. 2) and having conical cavity. Below the conical bag 1 there is a satellite bag 3 attached which is filled with the elution medium such as normal saline. The satellite bag 3 is connected to the conical bag 1 by means of a short capillary tube 4 (FIGS. 1 and 8) which is covered with a small ball 5 functioning as a ball valve. On a side of the satellite bag 3 there is a stopper arrangement 6 for the sterile infusion of medium into the bag 3. The rigid support 2 is also holding a collection bag 7 positioned above the conical bag 1. Both conical and collection bags have puncturing-type connector-arrangements 8 and 9 which allow aseptic connection and disconnection of these bags by means of a double-ended sterile needle connector 10. In order to hold the puncturing-type connector arrangement 8 in place there is an annular ring clamp 15 incorporated into the design of the rigid support 2 so that when the two halves are assembled the connector arrangement 8 is secured during subsequent operational steps. Both halves of the rigid support 2 are held together by an o-ring 11 which also functions as a snap-ring fitting into the groove 12 on the inner wall of the centrifuge bucket 13 and holding the rigid support 2 in its upper position within the centrifuge bucket. The indented configuration 14 shown at the lower end of the rigid support 2 is provided to prevent pinching of the bag 3 when the support 2 slides down and squeezes the bag 3.

Figure 2:
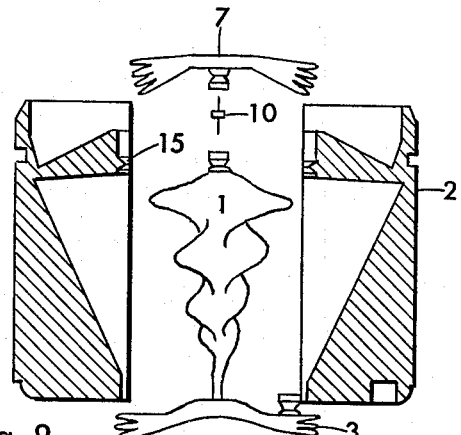
FIG. 2 is a vertical section of the apparatus taken along the vertical central axis and showing the apparatus in disassembled form and with empty bags.
Figure 3:
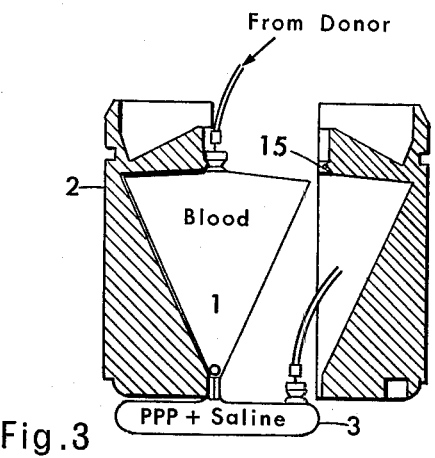
FIG. 3 is a vertical section of the apparatus taken along the vertical central axis and showing the apparatus in a partially assembled form and having two bags filled.
Figure 4:
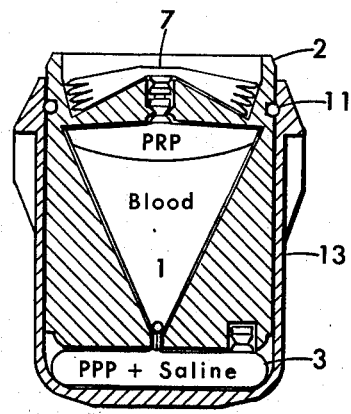
FIG. 4 is a vertical section of the apparatus taken along the vertical central axis and showing the apparatus being inserted into the centrifuge bucket and locked at the upper position in the bucket.
Figure 5:
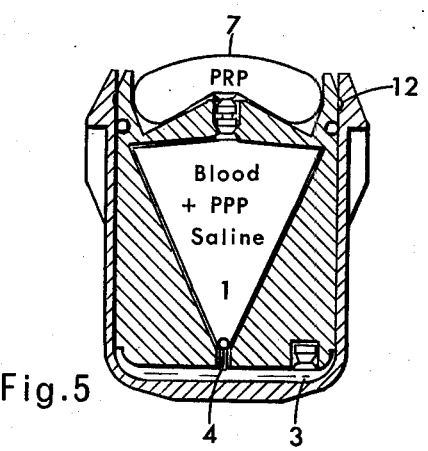
FIG. 5 is a vertical section of the apparatus taken along the vertical central axis and showing the apparatus at the lower position in the centrifuge bucket.
Figure 6:
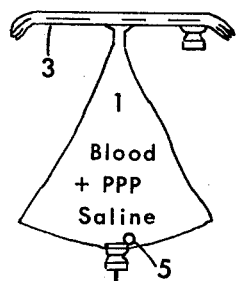
FIG. 6 is a vertical section of the centrifuge bucket containing an inserted bag taken along the vertical central axis and showing separation of PPP and PC in the bag.
Figure 7:
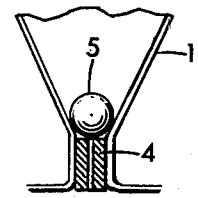
FIG. 7 is a vertical section of the conical bag together with its satellite bag taken along the vertical central axis and showing both bags in the inverted position with the blood reinfusion line connected.
Figure 8:
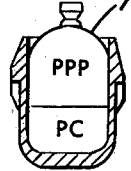
FIG. 8 is an enlarged fragmentary vertical central section through the capillary inlet port and a ball valve at the bottom of the conical bag.

The operational steps used in the separation of platelets with this system are illustrated in a diagrammatic series which is represented in FIG. 2 through FIG. 8. FIG. 2 shows a vertical sectional view of the device in unassembled form. All three bags, 3, 1 and 7, are shown empty and collapsed with the upper collection bag 7 being disconnected. In FIG. 3 is shown priming of the conical bag 1 with saline and PPP. The conical bag 1 is shown inserted in one-half of the rigid support 2. FIG. 4 shows an assembled system positioned inside the centrifugal bucket 13. The o-ring 11 which holds together both halves of the support 2 also holds the assembled support in the upper position of the centrifuge bucket where the o-ring 11 snaps into the groove 12 in the bucket 13. This holding arrangement allows one to subject the device to slow speed centrifugation, for instance at 500 rpm, for about one minute in order to clear the top of the chamber from blood cells. Thereafter the centrifugation speed is increased to about 2000 rpm at which the o-ring 11 is snapped off the groove 12 and the support 2 begins to slide down against the satellite bag 3, which forces saline through the capillary tube 4 into the conical bag 1. This action displaces PRP from the blood sample into the upper collection bag 7 as is illustrated in FIG. 5. Thereafter the collection bag 7 is disconnected, placed into a smaller bucket of another centrifuge (FIG. 6), and centifuged at high speed in order to obtain PC and PPP. PPP is then mixed with the blood remaining in the conical bag 1 (FIG. 7), and blood containing both saline and PPP is reinfused into the donor. FIG. 8 shows an enlarged sectional view of the capillary connector and the ball valve between the satellite bag 3 and conical bag 1.

The apparatus shown in FIGS. 9 and 10 is a version of a scaled-up system represented in FIG. 1 but incorporating only one collapsible bag 3 containing saline and having a conical separation chamber 17 housed inside the cylindrical body 18 which can move under centrifugal force inside the centrifuge bucket 13 and exerts pressure against the collapsible bag 3. The PRP receiving chamber 19 is sealed with the o-ring 20 to the cylindrical body 18 above the separation chamber 17. The device also has a needle valve 21 (FIG. 10) for the regulation of flow rate incorporated inside a modular insert 22 and having a nipple for connecting the collapsible bag 3.

FIG. 11 is a modular insert representing a possible version of an arrangement for delaying liquid flow during the start of centrifugation until maximal centrifugal force activates valve 23. It also incorporates needle valve 21 for controlling flow rate.

What is claimed is:

1. Apparatus for separating platelets from a blood sample comprising
   (a) a body adapted to be subjected to centrifugal force and containing a cavity with a volume of displacing liquid in the cavity,
   (b) a piston mounted in the body for movement into the cavity in response to centrifugal force on the piston with the piston containing a centrifugal chamber having inner and outer ends with a blood sample in the chamber from which platelets are to be withdrawn, and injection passageway means for movement of displacing liquid from the cavity to the centrifugal outer end of the chamber in response to movement of the piston into the cavity,
   (c) a discharge passageway at the centrifugally inner end of the chamber for discharging platelet rich plasma in response to injection of displacing liquid into the chamber,
   (d) a collapsible bag in the cavity surrounding the body of displacing liquid and communicating with the injection passageway means,
   (e) means for preventing flow of displacing liquid from the cavity to the chamber before centrifugal stratification of blood cells in the chamber.

2. The apparatus of claim 1 characterized further by the inclusion of a second bag containing the blood sample in the chamber and communicating with the collapsible bag in the cavity, and a third bag communicating through the discharge passageway with the second bag for receipt of platelet rich plasma.

3. A triple adapted to be received in a centrifugal apparatus for separating platelet rich plasma from a blood sample comprising
   (a) a central portion having a generally conical shape with a centrifugally outer end at the vertex of the cone and a centrifugally inner end at the opposite end thereof and adapted to containing the blood sample, (b) a collapsable injection portion adapted to contain a volume of saline less than the volume of the central portion of the bag and communicating with the centrifugally outer end of the central portion for injecting saline into the central portion as the injection portion collapses, and (c) an expandable collection portion communicating with the centrifugally inner end of the central portion for collecting platelet rich plasma displaced from the central portion.

* * * * *